US009206468B2

(12) United States Patent
Baker

(10) Patent No.: US 9,206,468 B2
(45) Date of Patent: Dec. 8, 2015

(54) ONE-STEP METHOD OF ELUTION OF DNA FROM BLOOD SAMPLES

(75) Inventor: Mei Wang Baker, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 48 days.

(21) Appl. No.: 13/328,189

(22) Filed: Dec. 16, 2011

(65) Prior Publication Data

US 2012/0156683 A1 Jun. 21, 2012

Related U.S. Application Data

(60) Provisional application No. 61/424,243, filed on Dec. 17, 2010.

(51) Int. Cl.
*C07H 21/00* (2006.01)
*C12Q 1/68* (2006.01)

(52) U.S. Cl.
CPC ................................ *C12Q 1/6806* (2013.01)

(58) Field of Classification Search
CPC ....................................................... C12Q 1/6806
USPC ........................................ 536/25.4; 435/6.12
See application file for complete search history.

(56) References Cited

U.S. PATENT DOCUMENTS

| 4,965,188 | A |  | 10/1990 | Mullis et al. |  |
|---|---|---|---|---|---|
| 5,231,015 | A | * | 7/1993 | Cummins et al. | 435/91.2 |
| 7,670,768 | B1 | * | 3/2010 | Heath et al. | 435/6.14 |
| 2003/0157492 | A1 |  | 8/2003 | Heath et al. |  |
| 2005/0032105 | A1 |  | 2/2005 | Bair et al. |  |
| 2005/0042656 | A1 | * | 2/2005 | Davis et al. | 435/6 |

FOREIGN PATENT DOCUMENTS

| WO | 0050564 |  | 8/2000 |
| WO | 2005007852 | A2 | 1/2005 |
| WO | 2011008814 | A2 | 1/2011 |
| WO | 2011137445 | A2 | 11/2011 |
| WO | 2012083175 | A1 | 6/2012 |

OTHER PUBLICATIONS

Chomczynski et al. Alkaline polyethylene glycol-based method for direct PCR from bacteria, eukaryotic tissue samples, and blood. BioTechniques 2006;40(4):454-8.*
Heath et al. Optimization of an automated DNA purification protocol for neonatal screening. Arch Pathol Lab Med 1999;123:1154-60.*
Baker et al. Development of a routine newborn screening protocol for severe combined immunodeficiency. J Allergy Clin Immunol 2009;124:522-7.*
Ye et al. An efficient procedure for genotyping single nucleotide polymorphisms. Nucleic Acids Research 2001;29(17):1-8.*
Adkins, et al.; "Utilizing Genomic DNA Purified From Clotted Blood Samples for Single Nucleotide Polymorphism Genotyping"; Arch Pathol Lab Med; 126; pp. 266-270; (2002).
Baker et al.; "Development of a Routine Newborn Screening Protocol for Severe Combined Immunodeficiency"; J Allergy Clin Immunol; 124(3); pp. 522-527; (2009).
de Vries, et al.; "Rapid Genotyping of Cytomegalovirus in Dried Blood Sports by Multiplex Real-Time PCR Assays Targeting the Envelope Glycoprotein gB and gH Genes"; Journal of Clinical Microbiology; 50(2); pp. 232-237; (2012); downloaded from http://jcm.asm.org/on Jan. 25, 2012 by Univ of Wisconsin—Mad.
Leruez-Ville, et al.; "Prospective Identification of Congenital Cytomegalovirus Infection in Newborns Using Real-Time Polymerase Chain Reaction Assays in Dried Blood Spots"; CID; 52; pp. 575-581; (2011); downloaded from cid.oxfordjournals.org by guest on Sep. 13, 2011.
Baker, Mei; "Development of One Step DNA Isolation from Dried Blood Newborn Screening Specimens"; Presentation at 2011 Newborn Screening and genetic Testing Symposium, San Diego, CA; Nov. 7-10, 2011.
Barbi et al., "Cytomegalovirus DNA detection in Guthrie cards: a powerful tool for diagnosing congenital infection", Journal of Clinical Virology 17, 2000, pp. 159-165.
Boppana et al., "Dried Blood Spot Real-time Polymerase Chain Reaction Assays to Screen Newborns for Congenital Cytomegalovirus Infection", JAMA, Apr. 14, 2010, vol. 303. No. 14, pp. 1375-1382.
Gohring et al., "Influence of difference-extraction methods and PCR techniques on the sensitivity of HCMV-DNA detection in dried blood spot (DBS) filter cards", Journal of Clinical Virology 48, 2010, pp. 278-281.
International Search Report and Written Opinion; PCT/US2011/065509; International Filing Date Dec. 16, 2011; Date of Mailing Mar. 28, 2012; 15 pages.
Klintschar, et al.; "Evaluation of an Alkaline Lysis Method for the Extraction of DNA from Whole Blood and Forensic Stains for STR Analysis"; Techical Notes; Journal of Forensic Sciences; 45(3); pp. 669-673; (2000).
Makowski et al.; "Enhanced Direct Amplification of Guthrie Card DNA Following Selective Elution of PCR Inhibitors"; Nucleic Acids Research; 23(18) pp. 3788-3789; (1995).
Rudbeck et al.; "Rapid, Simple Alkaline Extraction of Human Genomic DNA from Whole Blood, Buccal Epithelial Cells, Semen and Forensic Stains for PCR"; Biotechniques; 25(4); pp. 588-590, 592; (1998).
Buck et al.; "Design Strategies and Performance of Custom DNA Sequencing Primers"; BioTechniques; 27; pp. 528-536; 1999.
U.S. Appl. No. 13/327,977, filed Dec. 16, 2011; Final Office Action of Sep. 29, 2014; 38 pages.

* cited by examiner

*Primary Examiner* — Jezia Riley
(74) *Attorney, Agent, or Firm* — Cantor Colburn LLP

(57) ABSTRACT

Described are reagents, methods, and kits for eluting, and amplifying and/or characterizing DNA from liquid and dried blood samples. A one-step DNA elution buffer has been developed that simplifies purification of DNA from blood samples. The purified DNA is suitable for use in subsequent widely used techniques such as enzymatic DNA amplification and quantitative analysis such as real-time PCR.

18 Claims, 5 Drawing Sheets

Amplification Plot

Standard Curve Plot

SEQ ID NO: 23    C G A G T G G R T G G G G G G

SEQ ID NO: 24    C G A G T G G A T G G G G G G

SEQ ID NO: 25    C G A G T G G G T G G G G G G

SEQ ID NO: 25    C G A G T G G G T G G G G G G

ONE-STEP METHOD OF ELUTION OF DNA FROM BLOOD SAMPLES

CROSS-REFERENCE TO RELATED APPLICATIONS

The present application is a Nonprovisional of U.S. Provisional Application Ser. No. 61/424,243, filed on Dec. 17, 2010, the contents of which are incorporated herein in their entirety.

FIELD OF THE DISCLOSURE

The present disclosure is related to compositions and methods for the elution of DNA from blood samples.

BACKGROUND

Screening for disease is a paradigm of modern medical practice. In particular, newborn or neonatal screening is the practice of testing newborns for certain harmful or potentially fatal disorders that are not otherwise apparent at birth. Generally, blood drops are obtained from the heel, finger or the ear and then absorbed onto filter paper to produce a dried blood spot collection card, often referred to as a Guthrie card. The dried blood spots are tested for a variety of individual diseases and conditions, including those of metabolic, genetic, and/or hormonal origin. Because most of the United States mandate newborn screening, there is significant motivation, from both the economic and medical practice perspectives, for the development of rapid screening methods having a low overall cost. This testing saves millions of dollars per year in health care costs for treating people who would suffer the long-term effects of these disorders and diseases if not treated upon birth.

Many of the tests performed in routine newborn screening are tests that measure the enzymes or metabolites in blood by immunoreaction or tandem mass spectrometry, which correlate the markers to metabolic disorders. However, with the growing number of identified DNA biomarkers for genetic disorders, it is increasingly desirable to isolate DNA from blood samples in order to identify the DNA biomarkers therein, preferably in a high throughput multi-well format. The isolation of DNA from blood samples, especially dried blood samples, is generally a laborious process involving multiple buffers as well as multiple pipeting and aspiration steps which is not readily amenable to a high throughput format and automation. In addition, blood contains many contaminants such as lipids and proteins that can interfere with subsequent analysis steps, such as DNA amplification. The quality of the DNA extracted from blood is particularly important, for example, in the analysis of single copy number genes for which the signal to noise ratio is critically important.

What is needed are improved methods and kits for the extraction of DNA from blood samples.

BRIEF SUMMARY

In one aspect, a one step method of eluting DNA from a blood sample consists of adding a one-step elution buffer having a pH of about 9 to about 13 to the blood sample to form a mixture, heating the mixture at 90° C. to 99° C. for a time sufficient to elute the DNA from the blood sample to form an eluted DNA solution, and optionally cooling the eluted DNA solution at a temperature of at least about 4° C. for at least 5 minutes, wherein the eluted DNA solution is suitable for direct use in an enzymatic DNA amplification reaction.

In another aspect, a method of analyzing DNA from a blood sample consists essentially of adding a one-step elution buffer having a pH of about 9 to about 13 to the blood sample to form a mixture, heating the mixture at 90° C. to 99° C. for a time sufficient to elute the DNA from the blood sample to form an eluted DNA solution, optionally cooling the eluted DNA solution at a temperature of at least about 4° C. for at least 5 minutes, and analyzing the eluted DNA solution without further processing after elution.

In yet another aspect, a method of analyzing DNA from a plurality of blood samples consists essentially of disposing the each of the plurality of blood samples into a different well of a first multi-well plate, adding a one-step elution buffer having a pH of about 9 to about 13 to each well of the first multi-well plate to form a mixture in each well of the multi-well plate, heating the plurality of mixtures at 90° C. to 99° C. for a time sufficient to elute the DNA from the plurality of blood samples to form an eluted DNA solution in each well of the multi-well plate, optionally cooling the eluted DNA solution in each well of the multi-well plate at a temperature of at least about 4° C. for at least 5 minutes, and transferring each eluted DNA solution to a different well of a second multi-well plate without washing, wherein each well of the second multi-well plate contains a reaction mixture and primers for an enzymatic DNA amplification reaction, and performing an enzymatic DNA amplification reaction in each well of the second multi-well plate that contains an eluted DNA solution.

In a further aspect, a one-step DNA elution buffer consists of 2.5 to 10 mM KOH, 7.5 to 30 mM Tris base and 2.5 to 12.5 mM KCl, and wherein the pH is 11 to 12.

In another aspect, a kit for the elution of DNA from blood samples consists essentially of a one-step elution buffer having a pH of about 9 to about 13, a primer pair for amplification of a genetic marker, a standard for identification of the genetic marker or a set of calibrators for quantitation of gene copy numbers, and instructions for use.

Figure 1:
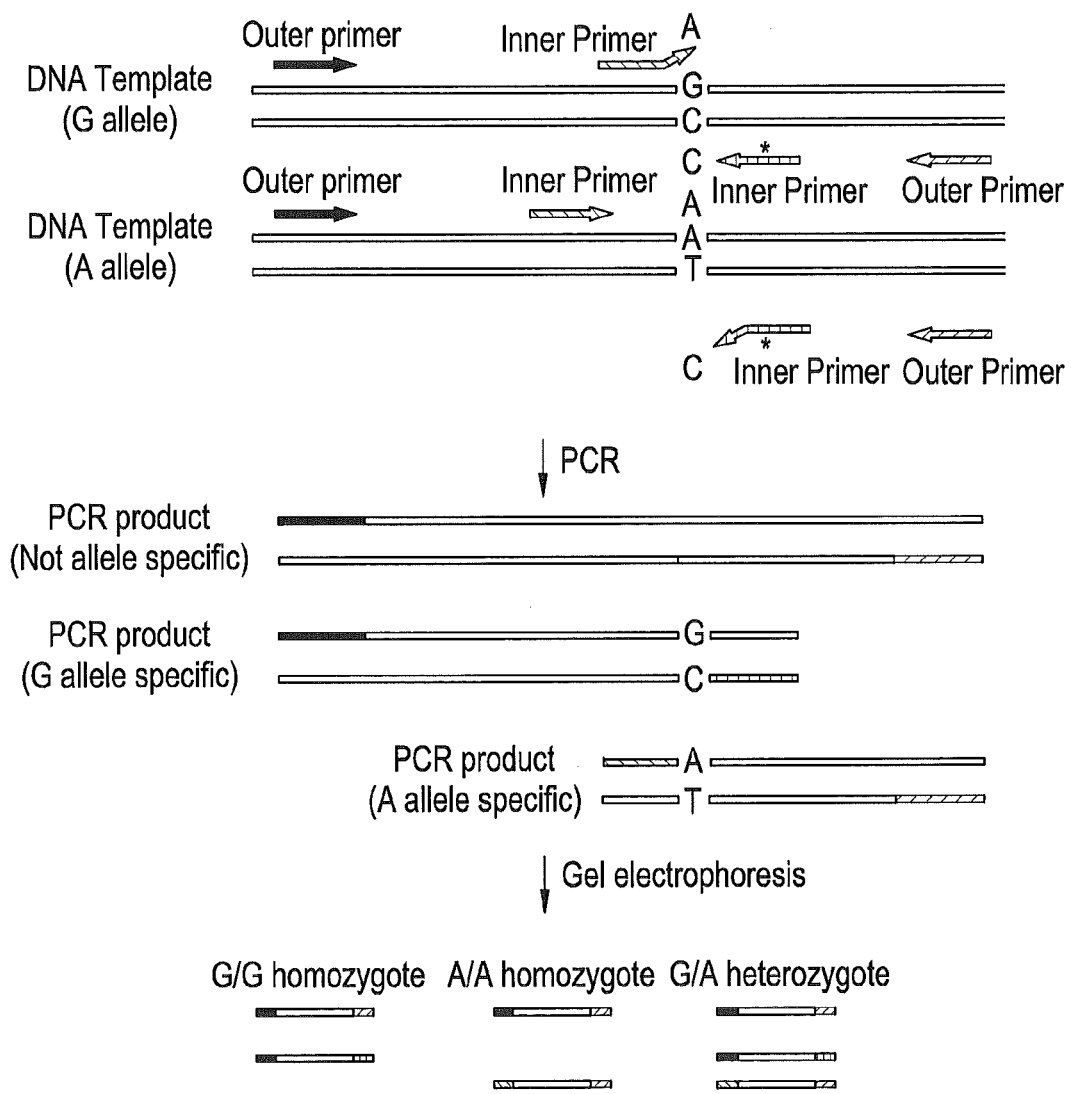
FIG. 1 is a schematic of a tetra-primer ARMS-PCR reaction used to detect GALT mutations.

The above-described and other features will be appreciated and understood by those skilled in the art from the following detailed description, drawings, and appended claims.

DETAILED DESCRIPTION

Described herein are reagents, methods, and kits for eluting, and amplifying and/or characterizing DNA from liquid and dried blood samples. The purified DNA is suitable for use in subsequent widely used techniques such as enzymatic DNA amplification and quantitative analysis such as real-time PCR.

The inventor of the present disclosure recently developed a genetic test that can identify those suffering from SCID, severe combined immunodeficiency disease or "bubble boy disease." This disease is characterized by defects in the T and B cell lymphocyte systems, leaving the person suffering from the disease highly susceptible to infections. These infections can escalate into life threatening conditions. If detected early, doctors understand what they are treating and parents can be aware of the infection risks. The most difficult steps in developing the test have involved reducing signal to noise problems. The DNA biomarker for SCID is called a T-cell receptor excision circle (TREC) generated by the DNA recombination process. TRECs do not replicate because they are episomal DNA circles. So TRECs are diluted out as cells undergo many divisions. It is imperative that enough DNA is eluted from the dried blood spot to ensure detection of low copy numbers of this DNA marker and that the eluted DNA has sufficient purity for further processing and analysis steps.

Unexpectedly, it was found that a method of eluting DNA from blood using a one-step elution buffer is sufficient to provide pure DNA for subsequent analysis such as an enzymatic DNA amplification reaction. The method described herein eliminates the numerous wash steps prior to and subsequent to eluting the DNA from the sample into solution that are included in prior art protocols. Unexpectedly, eliminating the wash steps has no detrimental effect on the signal-to-noise ratio and the DNA eluted in the one-step process can be used directly in subsequent enzymatic DNA amplification steps with no further purification. In addition, the optional agitation step aids to release the DNA from blood samples. The simplicity of the process described herein advantageously lends itself more readily to automation than prior art processes.

In one embodiment, a method of eluting DNA from a blood sample consists essentially of adding a one-step elution buffer to the blood sample to form a mixture, and heating the mixture for a time sufficient to elute the DNA from the blood sample to form an eluted DNA solution. Optionally, the eluted DNA solution is cooled at a temperature of at least about 4° C. for at least 5 minutes. As used herein, the term mixture includes solutions of liquid blood samples in the elution buffer as well as a dried blood sample suspended in the elution buffer. In another embodiment, a method of eluting DNA from a blood sample consists of adding a one-step elution buffer to the blood sample to form a mixture, and heating the mixture for a time sufficient to elute the DNA from the blood sample to form an eluted DNA solution. Heating is performed at a temperature of 90° C. to 99° C., specifically 94° C. to 99° C., and more specifically at 95° C. The time sufficient to elute the DNA is generally about 10 to about 40 minutes. The eluted sufficient to elute the DNA from the blood sample to form an eluted DNA solution, and analyzing the eluted DNA solution without further processing after elution such as washing or DNA solution is suitable for direct use in an enzymatic DNA amplification reaction. Heating is optionally performed with agitation. Optionally, the eluted DNA solution is cooled at a temperature of at least about 4° C. for at least 5 minutes. Optionally, the eluted DNA solution is centrifuged to remove particulates such as debris from dried blood filter paper.

In another embodiment, a method of analyzing DNA from a blood sample consists essentially of adding a one-step elution buffer to the blood sample to form a mixture, heating the mixture for a time without further processing after elution such as washing or the use of an additional buffer. In yet another embodiment, a method of analyzing DNA from a blood sample consists of adding a one-step elution buffer to the blood sample to form a mixture, heating the mixture for a time sufficient to elute the DNA from the blood sample to form an eluted DNA solution, and analyzing the eluted DNA solution without further processing after elution such as washing or the use of an additional buffer. Heating is optionally performed with agitation. Optionally, the eluted DNA solution is cooled at a temperature of at least about 4° C. for at least 5 minutes. Optionally, the eluted DNA solution is centrifuged to remove particulates such as debris from dried blood filter paper.

As used herein, the term consisting essentially of is meant to eliminate the use of additional washing steps and/or buffers during elution and prior to analysis. The advantage of this method is that with the addition of a one-step elution buffer and heating, a sufficient quality and quantity of DNA is produced for further analysis, such as, for example, a PCR reaction. Also, unexpectedly, the eluted DNA solution which contains DNA as well as the one-step elution buffer does not interfere with the enzymes used for DNA amplification when added to an amplification reaction. After elution of the DNA, the eluted DNA solution is optionally centrifuged to remove debris from dried blood filter paper and any particulate matter.

In another embodiment, a method of analyzing DNA from a plurality of blood samples consists essentially of disposing the each of the plurality of blood samples into a different well of a first multi-well plate, adding a one-step elution buffer to each well of the first multi-well plate to form a mixture in each well of the multi-well plate, heating the mixture for a time sufficient to elute the DNA from the plurality of blood samples to form an eluted DNA solution in each well of the multi-well plate, and transferring each eluted DNA solution to a well of a second multi-well plate without washing, wherein each well of the second multi-well plate contains a reaction mixture and primers for an enzymatic DNA amplification reaction, and performing an enzymatic DNA amplification reaction in each well of the second multi-well plate that contains an eluted DNA solution. Optionally, the eluted DNA solution is cooled at a temperature of at least about 4° C. for at least 5 minutes. In another embodiment, the method is performed in a single multi-well plate and the reaction mixture and primers for the enzymatic DNA amplification reaction are added to the eluted DNA solution in each well of the multi-well plate.

In one embodiment, the one-step elution buffer is Gentra® Elution Solution (Qiagen®), which has a pH of about 13. In another embodiment, the one-step elution buffer consists essentially of 5 to 22.5 mM potassium in the form of KOH, KCl, or a combination thereof, and 7.5 to 30 mM of a base having a buffering range of 7.0 to 9.5, wherein the pH of the one-step elution buffer is about 9 to about 13, specifically 10 to 13, and more specifically 11 to 12. In another embodiment, the one-step elution buffer consists of 5 to 22.5 mM potassium in the form of KOH, KCl, or a combination thereof, and 7.5 to 30 mM of a base having a buffering range of 7.0 to 9.5, wherein the pH of the one-step elution buffer is about 9 to about 13, specifically 10 to 13, and more specifically 11 to 12. In one embodiment, the base is Tris base, which has a buffering range of 7.0 to 9.2. Additional suitable buffers that buffer in a pH range of 7.0 to 9.5 include DIPSO (3-[N,N-bis (2-Hydroxyethyl)amino]-2-hydroxypropanesulfonic Acid Sodium Salt)(7.0-8.2), MOBS (3-(N-morpholino)propanesulfonic acid) (6.9-8.3), TAPSO (3-[N-Tris(hydroxymethyl) methylamino]-2-hydroxypropanesulfonic Acid)(7.0-8.2), HEPPSO (4-(2-Hydroxyethyl)piperazine-1-(2-hydroxypropanesulfonic acid) (7.1-8.5), POPSO (Piperazine- 1,4-bis(2-hydroxypropanesulfonic acid) dihydrate) (7.2-8.5), TEA (triethanolamine) (7.3-8.3), EPPS (4-(2-hydroxyethyl)

piperazine-1-propanesulfonic acid) (7.3-8.7), TRICINE (N-[Tris(hydroxymethyl)methyl]glycine, 3-[(3-Cholamidopropyl)dimethylammonio]propanesulfonic acid) (7.4-8.8), Glycylglycine (7.5-8.9), BICINE (N,N-Bis(2-hydroxyethyl)glycine) (7.6-9.0), HEPBS (N-(2-Hydroxyethyl) piperazine-N'(4-butanesulfonic acid) (7.6-9.0), TAPS (N-Tris(hydroxymethyl)methyl-3-aminopropanesulfonic Acid)(7.7-9.1), AMPD (2-Amino-2-methyl-1,3-propandiol) (7.8-9.7), TABS (N-tris[hydroxymethyl]methyl-4-aminobutanesulfonic acid) (8.2-9.6), AMPSO (N-(1,1-dimethyl-2-hydroxyethyl)-3-amino-2-hydroxy-propanesulfonic acid) (8.3-9.7), CHES (N-Cyclohexyl-2-aminoethanesulfonic acid) (8.6-10.0), and combinations thereof.

In another embodiment, the one-step elution buffer consists essentially of 2.5 to 10 mM KOH, 7.5 to 30 mM Tris base and 2.5 to 12.5 mM KCl. In another embodiment, the one-step elution buffer consists of 2.5 to 10 mM KOH, 7.5 to 30 mM Tris base and 2.5 to 12.5 mM KCl. In one embodiment, the one-step elution buffer consists of 5 mM KOH, 15 mM Tris base and 10 mM KCl and has a pH of 11 to 12.

During the research that led to the present disclosure, water and TE buffer were all tried as well as the buffers described in Example 4, but none of these buffers produced DNA of suitable quantity and quality as those described above. In addition, sodium was substituted for potassium, but did not produce satisfactory results.

The methods described herein are particularly suitable for the elution of DNA from blood samples. The blood sample is either a liquid blood sample or a dried blood sample. In one embodiment, a dried blood sample is a dried blood spot specimen on a filter paper card, also called a Guthrie card. In one embodiment, the sample is an approximately 3.2 mm in diameter disk punched from a blood sample dried on an adsorbent matrix such as a cellulose collection paper. In addition to the sample handling being very simple, there are further advantages to the use of dried blood samples. The stability of the blood sample poses no problem, and dried blood spots are easily stored. Furthermore any errors due to pipeting are circumvented. The results of the assays using the extracted DNA as described herein are furthermore not affected by differences in the sample quality or quantity.

In one embodiment, a dried blood sample is a sample from a newborn human. The traditional method for newborn testing starts with the collection of a small amount of blood from the newborn within the first postnatal days. The sample is adsorbed onto a piece of filter paper to provide a dried blood spot. This sample is sent to the laboratory, where a small disk, about 3 mm, is punched out from the spot for DNA extraction and analysis. The use of paper cards for the collection of blood samples is also particularly suitable for the storage and transportation of blood samples at the time of epidemiologic studies or for screening a population. Advantages of dried blood samples are the ease of collection, the low volume of storage, and the transport without need for refrigeration.

An exemplary elution method includes:
1. Add 30-60 μL of one-step elution buffer to a well of a 96-well plate containing a 3.2 mm dried blood disk.
2. Cover the plate.
3. Optionally centrifuge the plate at 3700 rpm for 5 minutes.
4. Heat the plate at 95° C. for 25 minutes.
5. Optionally, cool the eluted DNA solution at a temperature of at least about 4° C. for at least 5 minutes.
6. Optionally centrifuge the plate at 3700 rpm for 5 minutes.

Using the method disclosed herein, DNA of high yield and substantial purity can be obtained that is equivalent to that obtained using other more conventional methods requiring multiple washing steps. Preferably, the isolated DNA is substantially pure, which can be determined by being used in a variety of downstream analytical or diagnostic methods commonly encountered in the art, such as amplification, hybrization, sequencing, Southern blotting, enzymatic amplification reactions such as the polymerase chain reaction ("PCR"), microarray analysis, and the like. In a specific embodiment, the analysis is an enzymatic DNA amplification reaction.

PCR is an enzymatic amplification reaction used routinely to amplify one or more targeted nucleic acid sequences within a sample or mixture of nucleic acids. This process is disclosed in U.S. Pat. No. 4,965,188 to Mullis. For each target nucleic acid sequence to be amplified in this process, separate complementary strands of nucleic acid are treated with two primers selected to be substantially complementary to portions of the target nucleic acid within the two strands. A thermostable enzyme (a polymerase) is generally used to extend the primers to form complementary primer extension products. When these extension products are separated into their complementary strands, they serve as templates to extend the complementary primer into the target nucleic acid sequence. When separated, these target nucleic acid sequences in turn act as templates for synthesis of additional nucleic acid sequences. The PCR amplification process involves a series of simple steps. These include temperature cycling to cause hybridization of primers and templates, polymerase mediated synthesis of the primer extension products, and separation and subsequent annealing of the strands of template strands and the synthesized target nucleic acid sequences. Thus, there is an exponential increase in the amount of targeted nucleic acid sequences synthesized. PCR amplification is a very sensitive process. Therefore, a very high purity of starting sample is necessary.

Since the development of PCR, many variations of this enzymatic amplification have been developed, including allele-specific PCR for the detection of single nucleotide polymorphisms, asymmetric PCR in which one strand of a DNA hybrid is preferentially amplified, hot-start PCR, multiplex-PCR in which multiple primer sets are used to produce different sized amplicons in a single reaction, Tetra-primer ARMS-PCR, or a quantitative PCR reaction, for example.

In one embodiment, the analysis following DNA elution is a quantitative PCR reaction also called a real-time PCR analysis of the eluted DNA. The real-time polymerase chain reaction, also called quantitative real time polymerase chain reaction (Q-PCR/qPCR/qrt-PCR) or kinetic polymerase chain reaction (KPCR), is a laboratory technique based on the PCR, which is used to amplify and simultaneously quantify a targeted DNA molecule. It enables both detection and quantification (as absolute number of copies or relative amount when normalized to DNA input or additional normalizing genes) of one or more specific sequences in a DNA sample.

In one embodiment, the enzymatic amplification reaction contains primers for the amplification of a marker for a genetic disorder, such as a genetic disorder tested in newborn screening. Genetic disorders tested using DNA samples in new born screening include SCID, cystic fibrosis, Sickle Cell disease, and galactosemia. In one embodiment, the genetic disorder is SCID and the primers are SEQ ID NO: 13 and SEQ ID NO: 14. When the PCR reaction is a quantitative PCR reaction, the reaction also includes the probe of SEQ ID NO: 17.

In another embodiment, a kit for the amplification of DNA from a blood sample consists essentially of
  a one-step DNA elution buffer,
  a primer pair for amplification of a genetic marker, and a standard for identification of the genetic marker of a set of calibrators for quantitation of DNA copy numbers, and instructions for use.

By consisting essentially of, it is meant that the kit contains only the one-step elution buffer as described herein and contains no additional buffers such as wash buffers or other buffers for processing of DNA after elution. Instructions include the time and temperature for DNA elution, and a description of the primers and markers in the kit. In one embodiment, the kit includes markers and primers suitable for the detection of SCID, as described above.

The invention is further illustrated by the following non-limiting examples.

Example 1

DNA Elution from Dried Blood Samples Using a One-Step DNA Elution Buffer DNA Elution A. Place 3.2 mm dried blood punches one per well into the wells of a multi-well plate.
B. Add 54 μL of the one-step elution buffer into each well with an 8-Channel Pipette or an automatic liquid handler.
C. Cover the plate with an adhesive cover.
D. Centrifuge the plate at 3700 rpm for 5 minutes (optional).
E. Heat the plate at 95° C. or greater for 25 minutes. Optionally, the eluted DNA solution is cooled at a temperature of at least about 4° C. for at least 5 minutes.
F. Remove the plate from the thermal cycler, and allow the plate to cool to room temperature.

The one step buffer was: 15 mM Tris-Base, 10 mM KCl, and 5 mM KOH, pH 11.5.

After elution the solution is optionally centrifuged at 3700 rpm for 5 minutes before it is used in subsequent PCR reactions, however no additional solutions are added and no washing steps are performed.

Example 2

Galatose-1-phosphate Uridyltransferase (GALT) Mutation Detection in Eluted DNA Using Tetra-Primer ARMS-PCR Classic Galactosemia is an autosomal recessive inborn error of metabolism caused by deficiency of Galatose-1-phosphate Uridyltransferase (GALT). GALT gene targeted mutation analysis is performed as second tier testing after a GALT biochemical assay is done in newborn screening. The mutation panel includes p. Q188R, p. N134D, and p. S135L. With a Tetra-primer ARMS-PCR method, the internal control, wild type allele and mutant allele can be amplified simultaneously in a single reaction, and because of the applicons' difference in length, they can be distinguished by regular agarose gel electrophoresis. Tetra-primer ARMS-PCR is a hybrid of the tetra primer PCR method and the amplification refractory mutation system (ARMS). In Tetra-primer ARMS-PCR, both inner primers encompass a mutation at position-1 from the 3'-terminus which increases the specificity of ARMS-PCR. FIG. 1 is a schematic of the Tetra-primer ARMS-PCR methodology.

In the following Experiments, DNA eluted from 3.2 mm disks as in Example 1 was used. The PCR reaction mixes are given in Tables 1 and 2 and the PCR conditions in Table 3.

TABLE 1

| Reaction Mix: (25 μl) for Q188R, S315L | μl |
|---|---|
| 10X PCR Buffer | 2.5 |
| Forward inner primer (10 uM) | 2.5 |
| Reverse inner primer (10 uM) | 2.5 |
| Forward outer primer (1 uM) | 2.5 |
| Reverse outer primer (1 uM) | 2.5 |
| DNTPs (10 mM) | 0.5 |
| MgCl2 (25 mM) | 2.5 |
| H2O | 5 |
| Taq DNA Polymerase (5 U/I ul) | 0.5 |
| Genomic DNA—from an eluted DNA solution prepared as in Example 1 | 4 |

TABLE 2

| Reaction Mix: (25 μl) for N314D | μl |
|---|---|
| 10X PCR Buffer | 2.5 |
| Forward inner primer (1.7 uM) | 1 |
| Reverse inner primer (1.7 uM) | 1 |
| Forward outer primer (2.5 uM) | 1 |
| Reverse outer primer (2.5 uM) | 1 |
| DNTPs (10 mM) | 0.5 |
| MgCl2 (25 mM) | 2.5 |
| H2O | 11 |
| Taq DNA Polymerase (5 U/I ul) | 0.5 |
| Genomic DNA—from an eluted DNA solution prepared as in Example 1 | 4 |

TABLE 3

| PCR Condition: |
|---|
| 1. 95° C. for 5 min. |
| 2. 95° C. for 30 sec. |
| 3. 64° C. for 30 sec. |
| 4. 72° C. for 40 sec. |
| 5. Repeat 2-4 for 32 cycles |
| 6. 72° C. for 2 min. |
| 7. 4° C. forever |

TABLE 4

Primer Sequences

| Primer name | Sequence | SEQ ID NO: |
|---|---|---|
| Q188R (GALT) | | |
| Q188R-Inner-F | CTGTTCTAACCCCCACCCCCACTGACG | 1 |
| Q188R-Inner-R | CCCACTGGAGCCCCTGACACCCTTAACT | 2 |
| Q188R-Outer-F | AGTCACAGAGGAGCTGGGTGCCCAGTACC | 3 |
| Q188R-Outer-R | GGGGCAAAAGCAGAGAAGAACAGGCAGG | 4 |

TABLE 4-continued

Primer Sequences

| Primer name | Sequence | SEQ ID NO: |
|---|---|---|
| N314D (GALT) | | |
| N314D-Inner-F | CAGGATCAGAGGCTGGGGCCAACTTGG | 5 |
| N314D-Inner-R | GGGTAGTAATGAGCGTGCAGCTGCCAATGTTT | 6 |
| N314D-Outer-F | GGGTCGACGAGATGCTGGGACTGAGGGTGGAGCA | 7 |
| N314D-Outer-R | GGGGTCGACGCCTGCACATACTGCATGTGA | 8 |
| S135L (GALT) | | |
| S135L-Inner-F | GTAAGGTCATGTGCTTCCACCCCTGTTT | 9 |
| S135L-Inner-R | CGACATGAGTGGCAGCGTTACATACG | 10 |
| S135L-outer-F | GTGGCTAGACCTCTTGAGGGACTTCTGC | 11 |
| S135L-Outer-R | AGAACCAAAGCTTCATCACCCCCTCC | 12 |

PCR products were analyzed with 2% agarose gel electrophoresis (Agarose wide range standard 3:1, Sigma). Table 5 lists the mutations and the expected size of the PCR products formed in each for Wild type, Heterozygote, and Homozygote presentations.

TABLE 5

| GALT | Expected PCR Products and size (bp) | | |
|---|---|---|---|
| Mutation | Wild Type | Heterozygote | Homozygote |
| Q188R | 405, 276 | 405, 276, 184 | 405, 184 |
| N314D | 278, 431 | 431, 278, 212 | 431, 212 |
| S135L | 426, 288 | 426, 288, 192 | 426, 192 |

Figure 2:
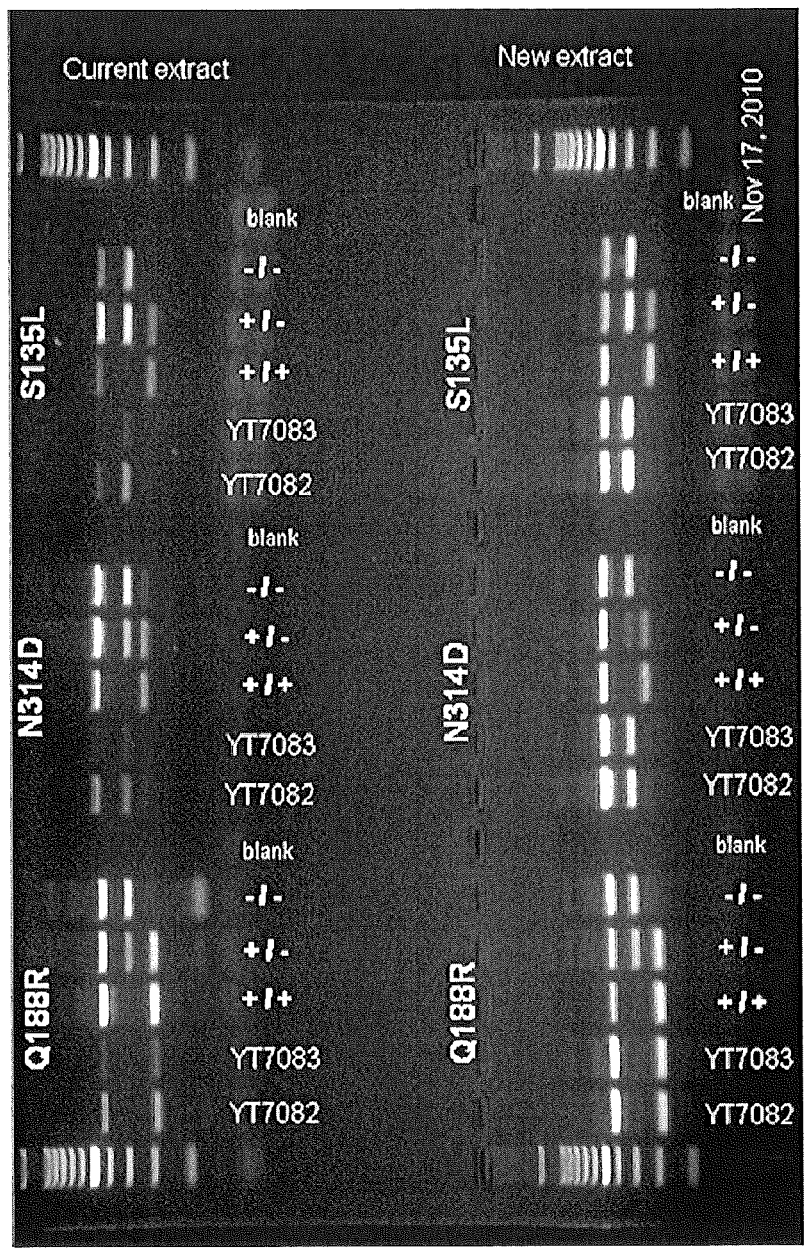
FIG. 2 shows GALT mutation detection using DNA eluted with a one-step elution buffer as disclosed herein (labeled as New extract).

FIG. 2 shows the results of the GALT mutation detection using DNA obtained by the method of Example 1 compared to a prior art method requiring multiple washing steps.
Lane 1. 100 bp Ladder
Lane 2. and 3. detected homozygous for Q188R
Lane 4. Control for Q188R homozygote
Lane 5. Control for Q188R heterozygote
Lane 6. Control for Q188R wild type
Lane 7. no target control
Lane 8. and 9. detected wild type for N314D
Lane 10. Control for N314D homozygote
Lane 11. Control for N314D heterozygote
Lane 12. Control for N314D wild type
Lane 13. no target control
Lane 14 and 15 detected wild type for S135L
Lane 16. Control for S135L homozygote
Lane 17. Control for S135L heterozygote
Lane 18. Control for S135L wild type
Lane 19. no target control
Lane 20. 100 bp Ladder The top panel are DNA samples prepared using a prior art multi-step elution protocol, while the bottom panel are DNA samples prepared using the one-step elution buffer of Example 1. The multi-step control elution process was:

DNA Extraction from DBS-Multiple Steps Method
A. Using an 8-Channel Pipette, add 90 µL of Qiagen® Gentra® DNA Purification Solution (Solution 1) to each well containing a 3.2 mm dried blood disk.
B. Centrifuge the plate at 3700 rpm for 30 seconds to ensure that the disks are immersed in the solution.
C. Incubate the plate at room temperature for 15 minutes.
D. Centrifuge the plate at 3700 rpm for 5 minutes.
E. Using an 8-Channel Pipette, remove and discard as much of the liquid as possible into 10% bleach solution.
F. Repeat step A-E, with Step C for 10 minutes.
G. Using an 8-Channel Pipette, add 90 µL of autoclaved Milli-Q H₂O to each well.
H. Centrifuge the plate at 3700 rpm for 30 seconds.
I. Using an 8-Channel Pipette, remove and discard as much liquid as possible into a 10% bleach solution.
J. Using an 8-Channel Pipette, add 24 µL Qiagen® Gentra® DNA Elution Solution (Solution 2) into each well.
K. Centrifuge the plate at 3700 rpm for 30 seconds and then cover with adhesive cover.
L. Place the plate in the −20° C. freezer for a minimum of 30 minutes.
M. Remove the plate from the freezer and allow it to thaw.
N. Centrifuge the plate. Allow the centrifuge to ramp up to 3700 rpm, wait 10-30 seconds, and stop the centrifuge. Remove the plate.
O. Place the plate into Veriti™ 96-Well Thermal Cycler.
P. Heat the plate at 99° C. for 30 minutes.
Q. After 99° C. incubation, remove the plate from the thermal cycler and allow the plate to cool to room temperature., remove the plate from the thermal cycler, and allow the plate to cool to room temperature.
R. Centrifuge the plate at 3700 rpm for 30 seconds.

As can be seen from FIG. 2, DNA eluted by the simplified one-step procedure from Example 1 allows for clean and accurate determination of GALT mutations. Moreover, one-step DNA outperformed multiple-steps DNA, as evidenced by successful amplification that would otherwise be a failure in the multiple-steps method.

Similar results were obtained using the Gentra® Elution Solution (Qiagen®) as the one step buffer.

Example 3

Real-time PCR Analysis for T-cell Receptor Excision Circles

Severe combined immunodeficiency (SCID) is a group of disorders caused by over a dozen single-gene defects that cause a defect in the development of normal naïve T cells. The inventor of the present application previously developed an assay for detecting SCID in newborns by quantitating T-cell excision circles (TRECs) in dried blood spots. TRECs are small, episomal pieces of DNA generated during the process of T-cell receptor rearrangement. The number of TRECs is a surrogate marker for the number of naïve T-cells that have migrated from the thymus, and all forms of SCID are characterized by low numbers of detectable TRECs. TRECs can be quantified using a real-time PCR method. Serially diluted plasmids containing known numbers of TRECs can be used to produce a calibration curve. A TREC cut-off level of 75 or less TRECs per 3.2 mm dried blood sample is used to identify newborns with SCID. The primers and probes used in the SCID assay are in Table 6. A β-actin primer pair serves as an optional control for DNA elution from the dried blood spots.

TABLE 6

| Primer name | Sequence | SEQ ID NO: |
|---|---|---|
| TREC forward primer | 5'-CACATCCCTTTCAACCATGCT-3' | 13 |
| TREC reverse primer | 5'-GCCAGCTGCAGGGTTTAGG-3' | 14 |
| β-actin forward primer | 5'-ATTTCCCTCTCAGGAATGGA-3' | 15 |
| β-actin reverse primer | 5'-CGTCACACTTCATGATGGAGTTG-3' | 16 |
| TREC PROBE | 6-FMA-ACACCTCTGGTTTTTGTAAAGGTGCCCACT-3'TAMRA | 17 |
| β-actin probe | 6-VIC-GTGGCATCCACGAAACTA-3'-TAMRA | 18 |

The reagents for the real-time PCR reaction were:

TABLE 7

| Reagents per reaction | μL |
|---|---|
| Gene Expression Master Mix | 10 |
| TREC forward primer (20 uM) | 0.5 |
| TREC reverse primer (20 uM) | 0.5 |
| Probe (15 uM) | 0.2 |
| BSA (10 mg/ml) | 0.8 |
| H$_2$O | 2 |
| DNA—from an eluted DNA solution prepared as in Example 1 | 6 |

The PCR reaction conditions were:

TABLE 8

Figure 3:
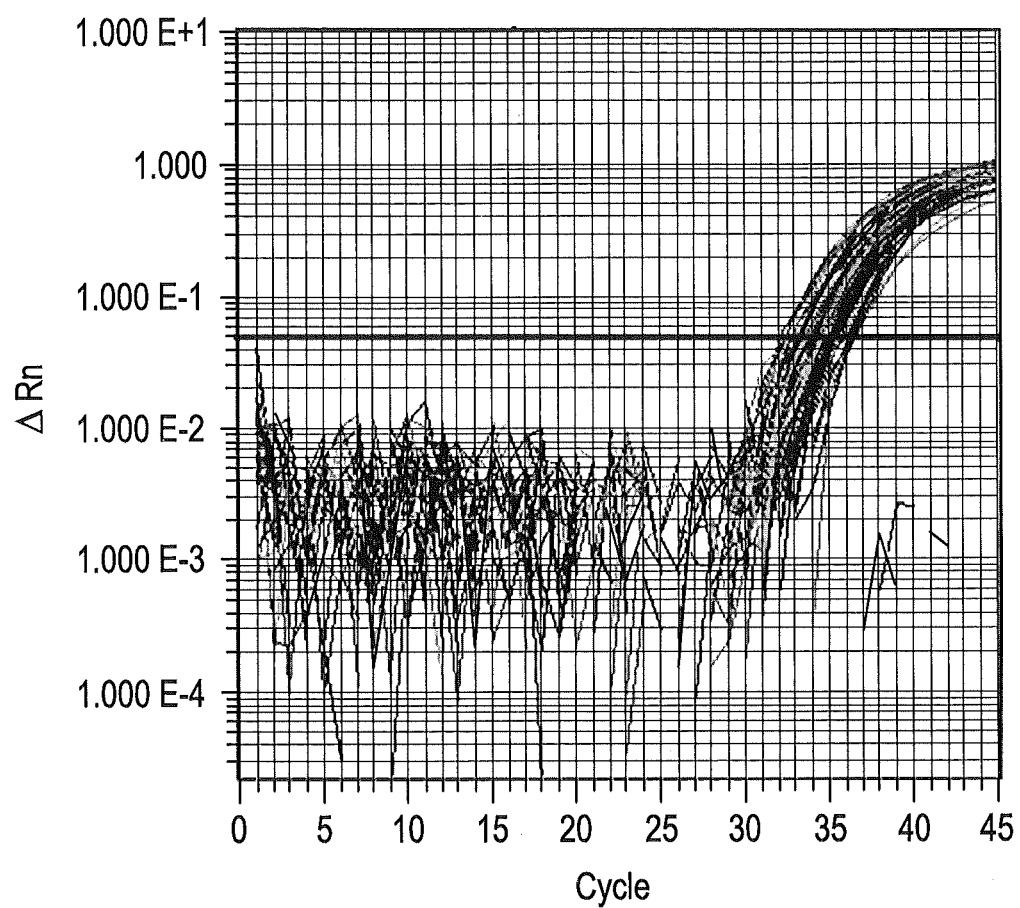
FIG. 3 shows the quantification of T-cell receptor excision circles (TRECs) by RT-qPCR.
Figure 4:
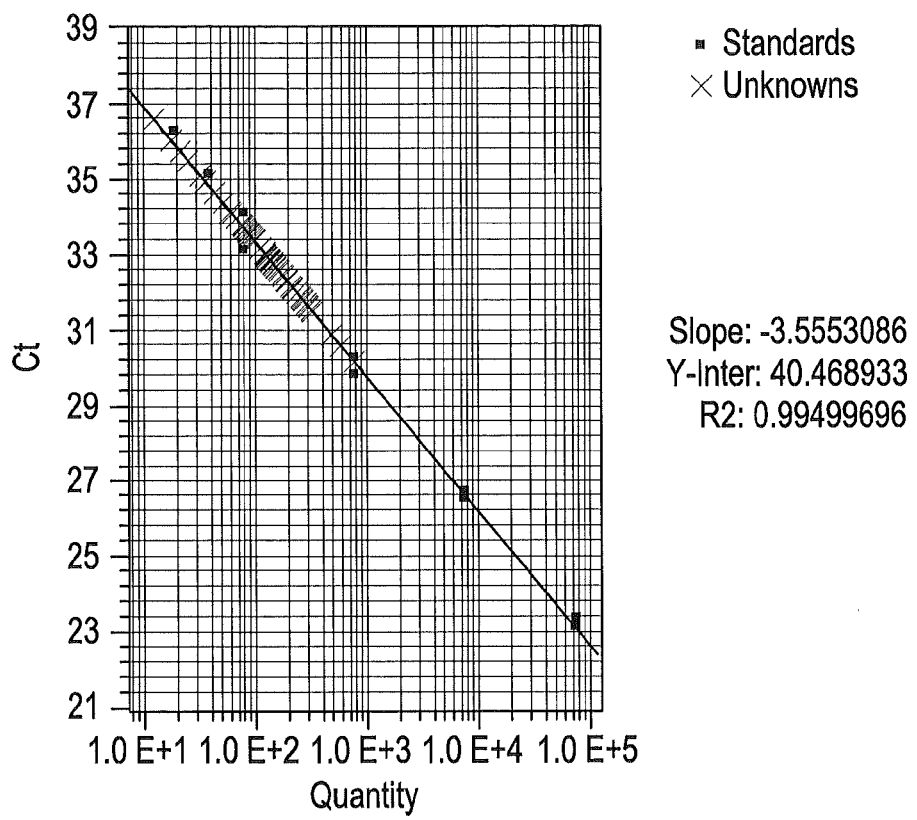
FIG. 4 shows the number of TRECs automatically determined based on serially diluted plasmids containing a known copy number of TRECs.

1. 50° C. for 2 min.
2. 95° C. for 10 min.
3. 95° C. for 30 sec.
4. 62° C. for 60 sec.
5. Repeat 3-4 for 40 cycles
6. 4° C. forever For data collection, a fixed cycle threshold (Ct) was set at the point when PCR amplification is still in the exponential phase. The cycle at which the instrument can discriminate the amplification generated fluorescence from the background noise is called the threshold cycle (Ct). FIG. 3 shows the successful RT-qPCR amplification plots for Quantification of T-cell Receptor Excision Circles (TREC) assay on DNA samples extracted by using the method described here. The number of TRECs are automatically determined based on serially diluted plasmids containing a known copy number of TRECs (FIG. 4).

Similar results were obtained using the Gentra® Elution Solution (Qiagen®) as the one step buffer.

Example 4

CF (Cystic Fibrosis Test)

Cystic fibrosis (also known as CF or mucoviscidosis) is an autosomal recessive genetic disease affecting most critically the lungs, and also the pancreas, liver, and intestine. CF is caused by mutations in the gene for the protein cystic fibrosis transmembrane conductance regulator (CFTR). Couples who are pregnant or planning a pregnancy can have themselves tested for the CFTR gene mutations to determine the risk that their child will be born with cystic fibrosis. In addition, newborn screening is often performed. The InPlex® CF Molecular Test is an in vitro diagnostic (IVD) that simultaneously tests for twenty-three separate mutations in the Cystic Fibrosis Transmembrane Receptor (CFTR) gene. In addition, the IVS8-5T/7T/9T markers are automatically reflexed as part of the test. Replacing the DNA extraction buffers with the, one-step buffer described in the present application allowed for successful identification of CFTR mutations as described below:

A. Prepare the PCR master mix following the instructions provided by the manufacture.

B. Aliquot 10.04 μL of the master mix into each PCR reaction tube.

B. Pipette 5.04 μL of DNA extract into its matching PCR reaction tube.

C. Place caps onto the PCR tubes and seal.

E. Place the PCR reaction tubes into the AB9700.

F. Begin thermal cycling following the instruction provided by the manufacture.

G. Remove the PCR reaction tubes from the AB9700.

H. Proceed to the Invader Reaction Procedure.

1. Carefully open the PCR reaction tubes.
2. Add 105 μL of the Invader Assay Reaction Mix to the PCR reaction tubes and pipette up and down 5-10 times to mix.
3. Transfer 105 μL of each of the specimen/Invader reaction mixtures to the loading ports on the InPlex® cards.
4. Centrifuge the cards two times at 1200 rpm for 1 minute (two separate 1 minute spins).
5. Seal the wells and ports of each card using a sealer.
6. Incubate the cards at 63.0° C. for 45 minutes in a hybridization oven
7. Remove cards from oven and allow cooling at room temperature for 2-4 minutes.

I. Load the card into TECAN Infinite 200 fluorometer for the card reading.
J. Obtain fluorescence counts using i-Control program.
K. Import fluorescence counts data into InPlex® program.
L. Record genotype information generated from InPlex® program.

Tested and correctly identified CF mutations

| | | | |
|---|---|---|---|
| ΔF508 | R117H | 3120 + 1G > A | R347P |
| R560T | 2184delA | 3659delC | W1282X |
| 2789 + 5G > A | R1162X | 621 + 1G > T | G542X |
| N1303K | A455E | 1717 − 1G > A | R553X |
| 3849 + 10kbC > T | 1898 + 1G > A | R334W | G85E |
| G551D | 711 + 1G > T | | |

The results shown herein demonstrate that good results can be obtained with a simple one-step DNA extraction procedure as described herein and that the more laborious methods generally used in the prior art are not necessary.

Example 4

RFLP Analysis

Figure 5:
FIG. 5 shows an RFLP analysis of the ACADM c. 985 A>G mutation by Nco I digestion.

PCR products extracted with the one-step buffer as described herein can be used for a restriction fragment length polymorphism (RFLP) analysis of the ACADM c. 985 A>G mutation by Nco I digestion. PCR products extracted with the one-step buffer as described herein can be used for a restriction fragment length polymorphism (RFLP) analysis of the ACADM c. 985 A>G mutation by NCO I digestion. Medium-chain acyl-CoA dehydrogenase deficiency (MCADD) is an inherited defect of fatty acid oxidation, causing sudden death in undiagnosed patients. Fatal outcomes can effectively be prevented by avoiding metabolic stress and following simple dietary management. Therefore, prospective newborn screening (NBS) is used for this condition. The 985 A>G mutation is the most prevalent alteration identified. The results of an RFLP assay wherein the DNA extraction was performed according to the present disclosure is shown in FIG. 5.

In the following Experiments, DNA eluted from 3.2 mm disks as in Example 1 was used.

The PCR reaction mixes are given in Tables 9, the PCR conditions are given in Table 10, and NCO I digestion mixes are given in Table 11.

TABLE 9

| PCR Reaction Mix: (25 μl) for ACADM c. 985 A > G mutation | |
|---|---|
| | μl |
| 10X PCR Buffer | 2.5 |
| Forward primer (10 uM) | 2.5 |
| Reverse primer (10 uM) | 2.5 |
| DNTPs (10 mM) | 0.5 |
| MgCl2 (25 mM) | 2.5 |
| H2O | 10 |
| Taq DNA Polymerase (5 U/I ul) | 0.5 |
| Genomic DNA—from an eluted DNA solution prepared as in Example 1 | 4 |

TABLE 10

| PCR Condition: |
|---|
| 1. 95° C. for 5 min.
2. 95° C. for 30 sec.
3. 64° C. for 30 sec.
4. 72° C. for 40 sec.
5. Repeat 2-4 for 32 cycles
6. 72° C. for 2 min.
7. 4° C. forever |

TABLE 11

| Nco I Digestion Reaction Mix: (15 μl) for ACADM c. 985 A > G mutation | |
|---|---|
| | μl |
| PCR product | 10 |
| NE Buffer 3 | 1.5 |
| Nco I | 1.0 |
| H2O | 2.5 |

The digestion reaction mixture is incubated at 37° C. for one hour.

TABLE 12

| Primer Sequences | | |
|---|---|---|
| Primer name | Sequence | SEQ ID NO: |
| 985 A>G (ACADM) | | |
| 985 A>G_F | TTTATGCTGGCTGAAATGGCCATG | 19 |
| 985 A>G_R | AGTTTTTCTACAGGATATTCTGTATTAAATCCATGGCCTC | 20 |

PCR products were analyzed with 2% agarose gel electrophoresis (Agarose wide range standard 3:1, Sigma). Table 13 lists the mutations and the expected size of the PCR products formed in each for Wild type, Heterozygote, and Homozygote presentations.

TABLE 13

| ACADM | Expected PCR Products and Their Size (bp) | | |
|---|---|---|---|
| Mutation | Wild Type | Heterozygote | Homozygote |
| 985 A > G | 178, 31* | 178, 158, 31* 20* | 158, 31*, 20* |

*These bands are very weak and may not be visualized in the gel.

The results shown herein demonstrate that good results can be obtained with a simple one-step DNA extraction procedure as described herein and that the more laborious methods generally used in the prior art are not necessary.

Example 6

Sequencing of the ACADSB c.1165 A>G Site

2-Methylbutyryl-CoA dehydrogenase deficiency, also known as short/branched-chain acyl-CoA dehydrogenase (SBCAD) deficiency, is a recently described autosomal recessive disorder of L-isoleucine metabolism. It is an inborn error of metabolism detectable by newborn screening.

Figure 6:
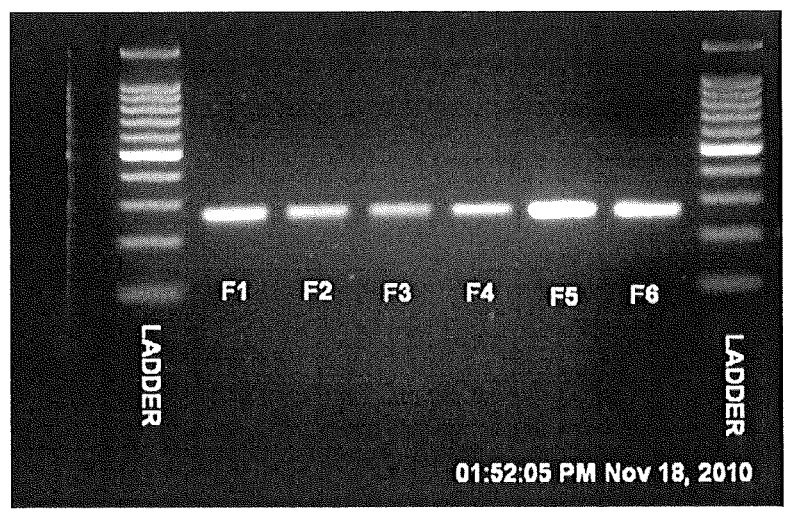
FIG. 6 shows the sequencing of a mutation in the ACADSB gene.
Figure 6:
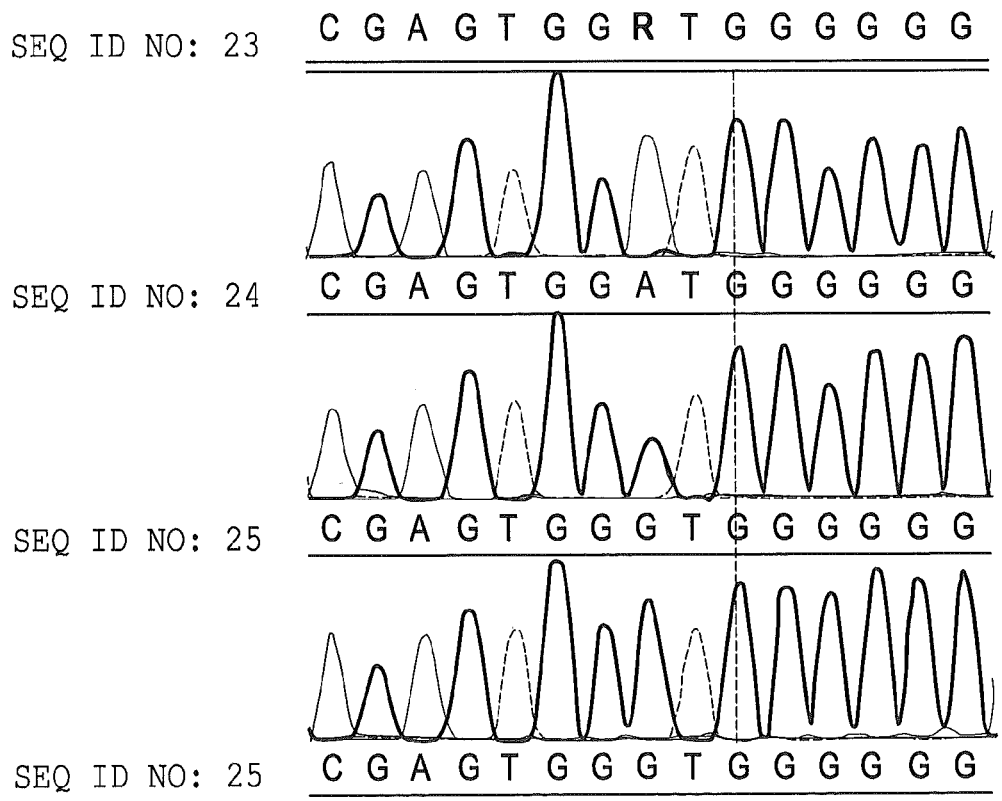

FIG. 6 shows successful sequencing using DNA prepared by the one-step method described herein. SEQ ID NO:23 is the sequence of the ACADSB 1165 region, SEQ ID NO:24 is the wild-type sequence and SEQ ID NO:25 is the c.1165 A>G site.

In the following Experiments, DNA eluted from 3.2 mm disks as in Example 1 was used.

The PCR reaction mixes are given in Tables 14, the PCR conditions are given in Tables 15, sequencing mixes are given in Tables 16, and sequencing reaction conditions are given in Tables 17.

TABLE 14

| PCR Reaction Mix: (25 µl) for ACADSB c.1165 A > G mutation | |
|---|---|
|  | µl |
| 10X PCR Buffer | 2.5 |
| Forward primer (10 uM) | 2.5 |
| Reverse primer (10 uM) | 2.5 |
| DNTPs (10 mM) | 0.5 |
| MgCl2 (25 mM) | 2.5 |
| H2O | 10 |
| Taq DNA Polymerase (5 U/I ul) | 0.5 |
| Genomic DNA—from an eluted DNA solution prepared as in Example 1 | 4 |

TABLE 15

| PCR Condition: |
|---|
| 1. 95° C. for 5 min. |
| 2. 95° C. for 30 sec. |
| 3. 64° C. for 30 sec. |
| 4. 72° C. for 40 sec. |
| 5. Repeat 2-4 for 32 cycles |
| 6. 72° C. for 2 min. |
| 7. 4° C. forever |

TABLE 16

| Sequencing Reaction Mixes | |
|---|---|
| Reagents | Volume (µL) |
| Terminator Ready Reaction Mix (TRR) | 2 |
| 5X Sequencing Buffer | 2 |
| 25 uM Forward OR Reverse Primer | 1 |
| DNA Template (PCR product) | 1 |
| H$_2$O | 4 |

TABLE 17

| Sequencing Reaction Condition: |
|---|
| 1. 96° C. for 1 min. |
| 2. 96° C. for 10 sec. |
| 3. 50° C. for 5 sec. |
| 4. 60° C. for 4 min. |
| 5. Repeat 2-4 for 25 cycles |
| 7. 4° C. forever |

TABLES 18

| Primers for ACADSB c.1165 A>G mutation | | |
|---|---|---|
| Primer name | Sequence | SEQ ID NO: |
| 1165 A>G (ACADSB) | | |
| 1165 A>G_F | tggagaatgggactgaagaga | 21 |
| 1165 A>G_R | caatctttgcatctcggaag | 22 |

Sequencing reaction products were purified by mixing with 45 µl of SAM Solution and 10 µl of XTerminator Solution, and loaded onto the 3130xl Genetic Analyzer. The run file generated from 3130xl Genetic Analyzer were further analyzed using DNASTAR Lasergene 8 to obtain sequence data.

The results shown herein demonstrate that good results can be obtained with a simple one-step DNA extraction procedure as described herein and that the more laborious methods generally used in the prior art are not necessary.

Example 7

Comparative Examples

A number of additional potential one-step elution buffers were tried and were found to be unsatisfactory based on no or low PCR amplification of the DNA.

10 mM Tris-Base
0.1 mM EDTA
0.1% Triton™ X-100
10 mM Tris-Base
0.1 mM EDTA
0.5% Triton™ X-100
1.2 mM KOH
10 mM Tris-Base
0,1 mM EDTA
1% Triton™ X-100
1.2 mM KOH
10 mM Tris-Base
0,1 mM EDTA
0.2% Triton X-100
25 mM NaOH
0.2 mM Na$_2$EDTA

| | | | |
|---|---|---|---|
| KOH | 10 mM | 5 mM | 2.5 mM |
| Tris-HCL | 30 mM | 15 mM | 7.5 mM |
| KCL | 10 mM | 5 mM | 2.5 mM |
| Betaine | 1M | 0.5 mM | 0.25 mM |

Triton™ X-100 is a surfactant of the formula (p-t-Octylphenoxy)polyethoxyethanol.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A one-step method of eluting DNA from a blood sample, consisting of
adding a one-step elution buffer to the blood sample to form a mixture, wherein the one-step elution buffer consists of 5 to 22.5 mM potassium in the form of KOH, KCl, or a combination thereof, and 7.5 to 30 mM of a base having a buffering range of 7.0 to 9.5, wherein the pH of the one-step elution buffer is 9 to 13,
heating the mixture at 90° C. to 99° C. for a time sufficient to elute the DNA from the blood sample to form an eluted DNA solution, and
optionally cooling the eluted DNA solution at a temperature of at least 4° C. for at least 5 minutes,
wherein the eluted DNA solution is suitable for direct use in an enzymatic DNA amplification reaction.

2. The method of claim 1, wherein the base having a buffering range of 7.0 to 9.5 is selected from the group consisting of Tris base, DIPSO (3-[N,N-bis(2-Hydroxyethyl)amino]-2-hydroxypropanesulfonic Acid Sodium Salt), MOPS (3-(N-morpholino)propanesulfonic acid), TAPSO (3-[N-Tris(hydroxymethyl)methylamino]-2-hydroxypropanesulfonic Acid), HEPPSO (4-(2-Hydroxyethyl)piperazine-1-(2-hydroxypropanesulfonic acid), POPSO (Piperazine-1,4-bis(2-hydroxypropanesulfonic acid) dihydrate), TEA (triethanolamine), EPPS (4-(2-hydroxyethyl)piperazine-1-propanesulfonic acid), TRICINE (N-[Tris(hydroxymethyl)methyl]glycine, 3-[(3-Cholamidopropyl)dimethylammonio]propanesulfonic acid), Glycylglycine, BICINE (N,N-Bis(2-hydroxyethyl)glycine), HEPBS (N-(2-Hydroxyethyl)piperazine-N'(4-butanesulfonic acid), TAPS (N-Tris(hydroxymethyl)methyl-3-aminopropanesulfonic Acid), AMPD (2-Amino-2-methyl-1,3-propandiol), TABS (N-tris[hydroxymethyl]methyl-4-aminobutanesulfonic acid), AMPSO (N-(1,1-dimethyl-2-hydroxyethyl)-3-amino-2-hydroxy-propanesulfonic acid), CHES (N-Cyclohexyl-2-aminoethanesulfonic acid), and combinations thereof.

3. The method of claim 1, wherein the one-step elution buffer consists of 2.5 to 10 mM KOH, 7.5 to 30 mM Tris base and 2.5 to 12.5 mM KCl, and wherein the pH is 11 to 12.

4. The method of claim 1, wherein the mixture is heated at 94° C. to 99° C.

5. The method of claim 1, wherein the blood sample is a dried blood sample on an adsorbent matrix.

6. A method of analyzing DNA from a blood sample, consisting essentially of
adding a one-step elution buffer to the blood sample to form a mixture, wherein the one-step elution buffer consists of 5 to 22.5 mM potassium in the form of KOH, KCl, or a combination thereof, and 7.5 to 30 mM of a base having a buffering range of 7.0 to 9.5, wherein the pH of the one-step elution buffer is 9 to 13,
heating the mixture at 90° C. to 99° C. for a time sufficient to elute the DNA from the blood sample to form an eluted DNA solution,
optionally cooling the eluted DNA solution at a temperature of at least 4° C. for at least 5 minutes, and
analyzing the eluted DNA solution without further processing after elution.

7. The method of claim 6, wherein analyzing the eluted DNA solution consists essentially of adding the eluted DNA solution directly to an enzymatic DNA amplification reaction.

8. The method of claim 7, wherein the enzymatic DNA amplification reaction is a quantitative PCR reaction or a multi-primer PCR reaction.

9. The method of claim 7, wherein the enzymatic DNA amplification reaction contains primers for the amplification of a marker for a genetic disorder.

10. The method of claim 9, wherein the genetic disorder is SCID and the primers are SEQ ID NO: 13 and SEQ ID NO: 14.

11. The method of claim 6, wherein the base having a buffering range of 7.0 to 9.5 is selected from the group consisting of Tris base, DIPSO (3-[N,N-bis(2-Hydroxyethyl)amino]-2-hydroxypropanesulfonic Acid Sodium Salt), MOPS (3-(N-morpholino)propanesulfonic acid), TAPSO (3-[N-Tris(hydroxymethyl)methylamino]-2-hydroxypropanesulfonic Acid), HEPPSO (4-(2-Hydroxyethyl)piperazine-1-(2-hydroxypropanesulfonic acid), POPSO (Piperazine-1,4-bis(2-hydroxypropanesulfonic acid) dihydrate), TEA (triethanolamine), EPPS (4-(2-hydroxyethyl)piperazine-1-propanesulfonic acid), TRICINE (N-[Tris(hydroxymethyl)methyl]glycine, 3-[(3-Cholamidopropyl)dimethylammonio]propanesulfonic acid), Glycylglycine, BICINE (N,N-Bis(2-hydroxyethyl)glycine), HEPBS (N-(2-Hydroxyethyl)piperazine-N'(4-butanesulfonic acid), TAPS (N-Tris(hydroxymethyl)methyl-3-aminopropanesulfonic Acid), AMPD (2-Amino-2-methyl-1,3-propandiol), TABS (N-tris[hydroxymethyl]methyl-4-aminobutanesulfonic acid), AMPSO (N-(1,1-dimethyl-2-hydroxyethyl)-3-amino-2-hydroxy-propanesulfonic acid), CHES (N-Cyclohexyl-2-aminoethanesulfonic acid), and combinations thereof.

12. The method of claim 6, wherein the one-step elution buffer consists of 2.5 to 10 mM KOH, 7.5 to 30 mM Tris base and 2.5 to 12.5 mM KCl, and wherein the pH is 11 to 12.

13. The method of claim 6, wherein the mixture is heated at 94° C. to 99° C.

14. The method of claim 6, wherein the blood sample is a dried blood sample on an adsorbent matrix.

15. A method of analyzing DNA from a plurality of blood samples consisting essentially of
 disposing the each of the plurality of blood samples into a different well of a first multi-well plate,
 adding a one-step elution buffer to each well of the first multi-well plate to form a mixture in each well of the multi-well plate, wherein the one-step elution buffer consists of 5 to 22.5 mM potassium in the form of KOH, KCl, or a combination thereof, and 7.5 to 30 mM of a base having a buffering range of 7.0 to 9.5, wherein the pH of the one-step elution buffer is 9 to 13,
 heating the plurality of mixtures at 90° C. to 99° C. for a time sufficient to elute the DNA from the plurality of blood samples to form an eluted DNA solution in each well of the multi-well plate,
 optionally cooling the eluted DNA solution in each well of the multi-well plate at a temperature of at least 4° C. for at least 5 minutes, and
 transferring each eluted DNA solution to a different well of a second multi-well plate without washing, wherein each well of the second multi-well plate contains a reaction mixture and primers for an enzymatic DNA amplification reaction, and
 performing an enzymatic DNA amplification reaction in each well of the second multi-well plate that contains an eluted DNA solution.

16. The method of claim 15, wherein the one-step elution buffer consists of 2.5 to 10 mM KOH, 7.5 to 30 mM Tris base and 2.5 to 12.5 mM KCl, and wherein the pH is 11 to 12.

17. The method of claim 14, wherein the mixture is heated at 94° C. to 99° C.

18. The method of claim 15, wherein the blood sample is a dried blood sample on an adsorbent matrix.

* * * * *

SEQUENCE LISTING

```
<160> NUMBER OF SEQ ID NOS: 25

<210> SEQ ID NO 1
<211> LENGTH: 27
<212> TYPE: DNA
<213> ORGANISM: Artificial Sequence
<220> FEATURE:
<223> OTHER INFORMATION: primer

<400> SEQUENCE: 1
ctgttctaac ccccaccccc actgacg                                       27

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
cccactggag cccctgacac ccttaact                                      28

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
agtcacagag gagctgggtg cccagtacc                                     29

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
```

```
ggggcaaaag cagagaagaa caggcagg                                          28

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
caggatcaga ggctggggcc aacttgg                                           27

<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6
gggtagtaat gagcgtgcag ctgccaatgt tt                                     32

<210> SEQ ID NO 7
<211> LENGTH: 34
<212> TYPE: DNA
<213> ORGANISM: Artificial Sequence
<220> FEATURE:
<223> OTHER INFORMATION: primer

<400> SEQUENCE: 7
gggtcgacga gatgctggga ctgagggtgg agca                                   34

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ggggtcgacg cctgcacata ctgcatgtga                                        30

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
gtaaggtcat gtgcttccac ccctgttt                                          28

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
cgacatgagt ggcagcgtta catacg                                            26

<210> SEQ ID NO 11
<211> LENGTH: 28
<212> TYPE: DNA
```

```
<213> ORGANISM: Artificial Sequence
<220> FEATURE:
<223> OTHER INFORMATION: primer

<400> SEQUENCE: 11
gtggctagac ctcttgaggg acttctgc                                              28

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
agaaccaaag cttcatcacc ccctcc                                                26

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
cacatccctt tcaaccatgc t                                                     21

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
gccagctgca gggtttagg                                                        19

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
atttccctct caggaatgga                                                       20

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
cgtcacactt catgatggag ttg                                                   23

<210> SEQ ID NO 17
<211> LENGTH: 30
<212> TYPE: DNA
<213> ORGANISM: Artificial Sequence
<220> FEATURE:
<223> OTHER INFORMATION: probes

<400> SEQUENCE: 17
acacctctgg ttttttgtaaa ggtgcccact                                           30
```

<210> SEQ ID NO 18
<211> LENGTH: 18
<212> TYPE: DNA
<213> ORGANISM: Artificial Sequence
<220> FEATURE:
<223> OTHER INFORMATION: probes

<400> SEQUENCE: 18
gtggcatcca cgaaacta                                                       18

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
tttatgctgg ctgaaatggc catg                                                24

<210> SEQ ID NO 20
<211> LENGTH: 40
<212> TYPE: DNA
<213> ORGANISM: Artificial Sequence
<220> FEATURE:
<223> OTHER INFORMATION: primer

<400> SEQUENCE: 20 agttttcta caggatattc tgtattaaat ccatggcctc                                40

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
tggagaatgg gactgaagag a                                                   21

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
caatctttgc atctcggaag                                                     20

<210> SEQ ID NO 23
<211> LENGTH: 15
<212> TYPE: DNA
<213> ORGANISM: Homo sapiens
<220> FEATURE:
<221> NAME/KEY: misc_feature
<222> LOCATION: (8)..(8)
<223> OTHER INFORMATION: r= a or g

<400> SEQUENCE: 23
cgagtggrtg ggggg                                                          15

<210> SEQ ID NO 24
<211> LENGTH: 15
<212> TYPE: DNA

```
<213> ORGANISM: Homo sapiens

<400> SEQUENCE: 24
cgagtggatg ggggg                                                    15

<210> SEQ ID NO 25
<211> LENGTH: 15
<212> TYPE: DNA
<213> ORGANISM: Homo sapiens

<400> SEQUENCE: 25
cgagtgggtg ggggg                                                    15
```